(12) United States Patent
Full (10) Patent No.: US 7,485,861 B2
(45) Date of Patent: Feb. 3, 2009

(54) SYSTEM AND METHOD FOR REMOTE EMISSIONS SENSING INCLUDING CALCULATION AND CALIBRATION TECHNIQUES COMPENSATING FOR TEMPERATURE AND PRESSURE EFFECTS

(75) Inventor: Gary Full, Tucson, AZ (US)

(73) Assignee: Environmental Systems Products Holdings Inc., East Granby, CT (US)

( * ) Notice: Subject to any disclaimer, the term of this patent is extended or adjusted under 35 U.S.C. 154(b) by 181 days.

(21) Appl. No.: 11/053,334

(22) Filed: Feb. 9, 2005

(65) Prior Publication Data

US 2005/0197794 A1    Sep. 8, 2005

Related U.S. Application Data (60) Provisional application No. 60/542,402, filed on Feb. 9, 2004.

(51) Int. Cl.
*G01N 21/00* (2006.01)
(52) U.S. Cl. .................... 250/338.5; 250/346
(58) Field of Classification Search .............. 250/338.5, 250/346
See application file for complete search history.

(56) References Cited

U.S. PATENT DOCUMENTS

| | | | |
|---|---|---|---|
| 3,593,023 A | 7/1971 | Dodson et al. | |
| 3,957,372 A | 5/1976 | Jowett et al. | |
| 3,958,122 A | 5/1976 | Jowett et al. | ................ 250/346 |
| 3,973,848 A | 8/1976 | Jowett et al. | |
| 4,160,373 A | 7/1979 | Fastaia et al. | |
| 4,204,768 A | 5/1980 | N'Guyen | |
| 4,417,467 A | 11/1983 | Higgs et al. | |
| 4,561,786 A | 12/1985 | Anderson | |
| 5,167,146 A | 12/1992 | Hostetter | |
| 5,210,702 A | 5/1993 | Bishop et al. | ................ 364/496 |
| 5,319,199 A | 6/1994 | Stedman et al. | .......... 250/338.5 |
| 5,343,043 A | 8/1994 | Johnson | |
| 5,369,976 A | 12/1994 | Ratton | |
| 5,371,367 A | 12/1994 | DiDomenico et al. | |
| 5,388,453 A | 2/1995 | Ratton et al. | |
| 5,401,967 A | 3/1995 | Stedman et al. | .......... 250/338.5 |
| 5,418,366 A | 5/1995 | Rubin et al. | |
| 5,489,777 A | 2/1996 | Stedman et al. | |
| 5,498,872 A | 3/1996 | Stedman et al. | |
| 5,543,113 A | 8/1996 | Koike et al. | |
| 5,563,420 A | 10/1996 | Sullivan et al. | |
| 5,583,765 A | 12/1996 | Kleehammer | |
| 5,591,975 A | 1/1997 | Jack et al. | ................ 250/338.5 |
| 5,621,166 A | 4/1997 | Butler | |
| 5,644,133 A | 7/1997 | DiDomenico et al. | |
| 5,719,396 A | 2/1998 | Jack et al. | |
| 5,726,450 A | 3/1998 | Peterson et al. | .......... 250/338.5 |

(Continued)

FOREIGN PATENT DOCUMENTS

CA    2093998    7/1999

(Continued)

*Primary Examiner*—David P Porta
*Assistant Examiner*—Shun Lee
(74) *Attorney, Agent, or Firm*—Pillsbury Winthrop Shaw Pittman LLP (57) ABSTRACT

A remote emissions sensing (RES) system and method for measuring the exhaust gas composition of a motor vehicle is provided, including calibration methodologies for compensating for the effects of ambient temperature and/or pressure.

6 Claims, 5 Drawing Sheets

U.S. PATENT DOCUMENTS

| | | |
|---|---|---|
| 5,739,413 A | 4/1998 | Kohn et al. |
| 5,797,682 A | 8/1998 | Kert et al. .................. 374/123 |
| 5,831,267 A | 11/1998 | Jack et al. ............... 250/338.5 |
| 5,835,871 A | 11/1998 | Smith et al. |
| 5,884,226 A | 3/1999 | Anderson et al. |
| 5,916,294 A | 6/1999 | Naber et al. |
| 6,230,087 B1 | 5/2001 | DiDomenico et al. |
| 6,286,360 B1 | 9/2001 | Drzewiecki |
| 6,307,201 B1 | 10/2001 | DiDomenico et al. |
| 6,455,851 B1 | 9/2002 | Lord et al. |
| 6,560,545 B2 | 5/2003 | Stedman et al. |
| 6,561,027 B2 | 5/2003 | Rendahl et al. |
| 6,671,630 B2 | 12/2003 | Stedman et al. |
| 6,701,256 B2 | 3/2004 | Stedman et al. |
| 6,723,989 B1 | 4/2004 | DiDomenico et al. |
| 6,744,059 B2 | 6/2004 | DiDomenico et al. |
| 6,744,516 B2 | 6/2004 | DiDomenico et al. |
| 6,750,444 B2 | 6/2004 | Rendahl et al. |
| 6,757,607 B2 | 6/2004 | Rendahl et al. |
| 6,781,110 B2 | 8/2004 | Rendahl et al. |
| 6,789,021 B2 | 9/2004 | Rendahl et al. |
| 6,833,922 B2 | 12/2004 | DiDomenico et al. |
| 6,841,778 B1 | 1/2005 | Shifflett et al. |
| 6,900,893 B2 | 5/2005 | Foley et al. |
| 6,983,639 B1 | 1/2006 | DiDomenico et al. |
| 7,016,789 B2 | 3/2006 | Stedman et al. |
| 2002/0052698 A1 | 5/2002 | DiDomenico et al. |
| 2003/0089854 A1 | 5/2003 | Shifflett et al. |
| 2003/0120434 A1 | 6/2003 | DiDomenico et al. |
| 2004/0155191 A1 | 8/2004 | Stedman et al. |

FOREIGN PATENT DOCUMENTS

| | | |
|---|---|---|
| CA | 2131865 | 6/2000 |
| CN | 1253624 A | 5/2000 |
| GB | 2219397 | 12/1989 |
| GB | 2 386 415 | 9/2003 |
| WO | WO 00/34755 | 6/2000 |
| WO | WO 0282059 A1 * | 10/2002 |
| WO | WO 03/078982 | 9/2003 |

* cited by examiner

VIEW 1000

Ambient Path Temp: [ ] default = 20 deg. C.

Ambient Path Pressure: [ ] 13.6 Psia (default)

Internal Cell Temp: [ ] default = ambient + 8 deg. C.

Internal Cell Pressure: [ ]

Plume Temp: [ ] ⎫
Plume Pressure: [ ] ⎬ From Instrumentation

Additional Point "n"
Temp: [ ]
Pressure: [ ]

$CO_2$ Temp. { A2: [ ]  A1: [ ]  A0: [ ] }

CO Temp. A0: [ ]

$CO_2$ Pressure { A2: [ ]  A1: [ ]  A0: [ ] }

CO Pressure { A2: [ ]  A1: [ ]  A0: [ ] }

SYSTEM AND METHOD FOR REMOTE EMISSIONS SENSING INCLUDING CALCULATION AND CALIBRATION TECHNIQUES COMPENSATING FOR TEMPERATURE AND PRESSURE EFFECTS

CROSS-REFERENCE TO RELATED APPLICATIONS

This application claims priority to U.S. Provisional Patent Application Ser. No. 60/542,402, filed Feb. 9, 2004, which is incorporated herein by reference in its entirety.

FIELD OF THE INVENTION

The invention relates generally to a remote emissions sensing (RES) system and method including calculation and calibration techniques (or methodologies) to compensate for temperature and pressure effects.

BACKGROUND OF THE INVENTION

Systems and methods for remotely monitoring the exhaust gas composition of motor vehicles are known. Examples of such systems and methods are described in, for example, U.S. Pat. Nos. 5,210,702, 5,319,199, 5,401,967, 5,591,975, 5,726,450, 5,797,682, and 5,831,267, each of which is hereby incorporated herein by reference in its entirety. Commercial systems such as the AccuScan™ Remote Sensing Device (RSD) 3000 and the AccuScan™ Remote Sensing Device (RSD) 4000 offered by Environmental Systems Products, Inc. are also known.

Despite steady advances in the sophistication and robustness of remote emissions sensing (RES) systems, many RES systems remain susceptible to erroneous readings or inconsistent results. Unfortunately, such drawbacks can sometimes lead to relatively high incidences of discarded data or relatively high incidences of "flagged" test results, which indicate suspect results. These and other problems can reduce the benefits of an RES system.

SUMMARY OF THE INVENTION

Various aspects of the invention disclosed herein overcome drawbacks associated with various, existing RES systems by recognizing that absorption coefficients of gases (e.g., CO and $CO_2$) change as the temperature and pressure of the gases change, and then compensating for those changes. In other words, a fixed number of molecules (e.g., $CO_2$ molecules) of a gas in a measurement path will measure differently as ambient conditions, particularly temperature and pressure, change. As such, a different gas curve (e.g., number of molecules versus transmittance) exists at each ambient temperature and pressure condition. This recognition signifies a departure from conventional calibration methodologies and calculation techniques used with known RES systems.

Having recognized the effect that changes in ambient conditions have on absorption coefficients of gases, the invention disclosed herein further overcomes drawbacks associated with existing RES systems by correcting or compensating for changes in ambient pressure and/or temperature when measuring gases.

One advantage provided by the invention is improved accuracy of calibration or compensation curves (e.g., number of molecules versus transmittance) that define gas relationships at various gas temperature and/or pressure conditions. As such, the amount of one or more molecular species of interest in an exhaust plume may be more accurately measured.

These and other objects, features, and advantages of the invention will be apparent through the detailed description of the preferred embodiments and the drawings attached hereto. It is also to be understood that both the foregoing general description and the following detailed description are exemplary and not restrictive of the scope of the invention.

DETAILED DESCRIPTION OF THE INVENTION

An overview of a remote emissions sensing (RES) system is first provided, followed by a discussion of the calculation and calibration techniques (or methodologies) of the invention which are utilized to compensate for temperature and pressure effects.

Figure 1:
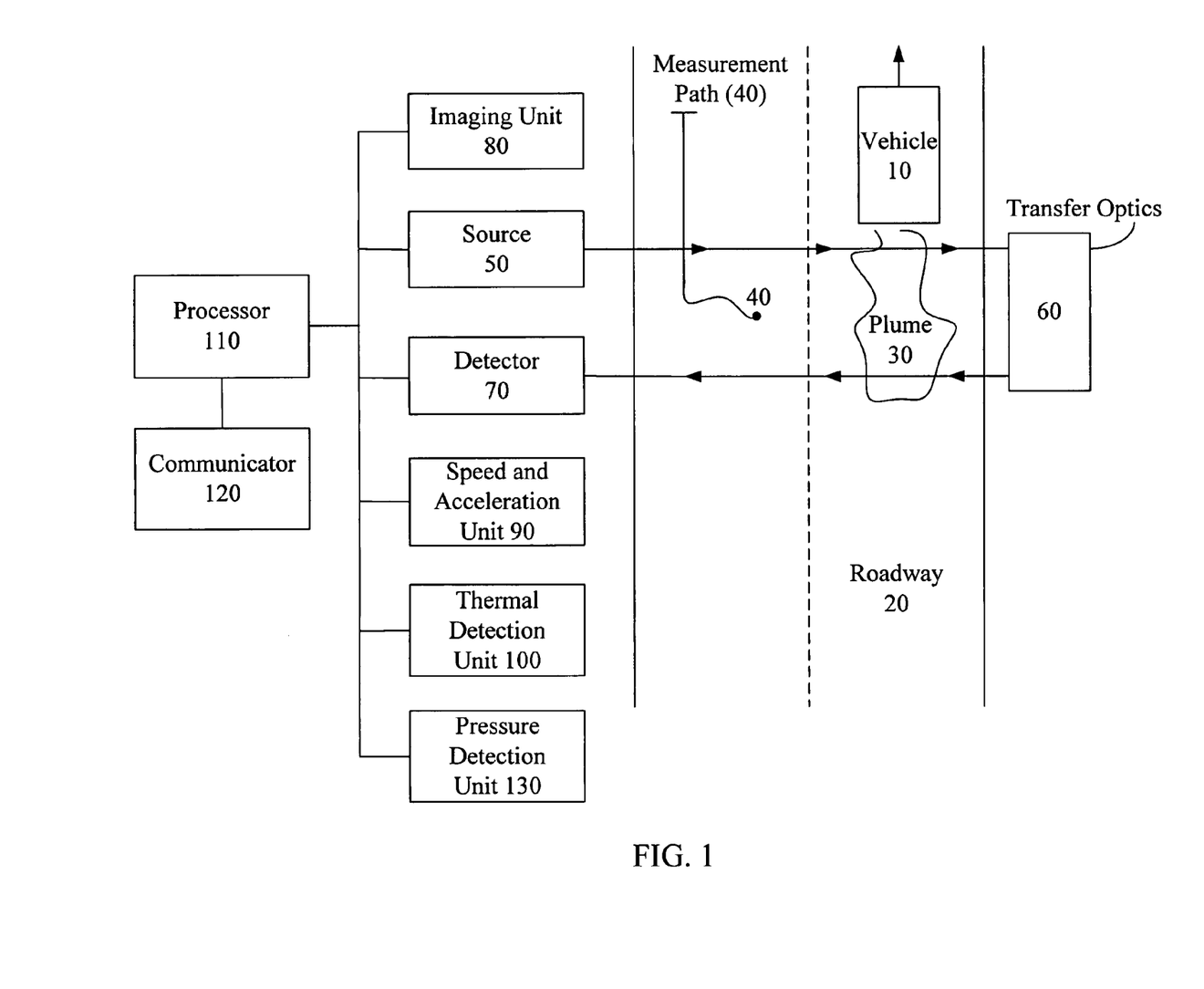
FIG. 1 is an exemplary illustration of a remote emissions sensing (RES) system, according to an embodiment of the invention.

FIG. 1 is an exemplary illustration of a RES system, according to an embodiment of the invention. The compensation techniques disclosed herein can be used with this or other system configurations. Embodiments of the invention may include some or all of the RES system components as described below, or other components.

According to one implementation, the RES system measures emissions in an exhaust plume 30 (from a motor vehicle 10) in a measurement path 40 on a roadway 20. Roadway 20 may comprise a single or multi-lane roadway, or any other roadway or driving surface suitable for the safe passage of vehicle 10 under various operating conditions. Alternatively, roadway 20 may comprise a test lane designated for vehicle emissions testing, wherein vehicle 10 may be tested under a variety of operating conditions.

In one embodiment, the RES system may comprise one or more sources of electromagnetic radiation (ER) 50 which may be used in the absorption spectroscopy measurement of various components of vehicle exhaust emissions in a known manner. Source 50 may comprise an infrared (IR) radiation source. In alternative embodiments, other types of radiation sources may be used including, for example, an ultraviolet (UV) source, a visible light source, or other suitable sources as known and understood by those having skill in the art. In some embodiments, a combination of radiation sources may be used.

The RES system may further comprise one or more detectors or a detector array 70 for detecting radiation in a known manner. Detector array 70 is preferably chosen to permit detection of electromagnetic radiation emitted by source 50. For example, detector array 70 may comprise a photodetector (e.g., a photodiode), a photomultiplier tube (PMT), a spectrometer, or any other suitable radiation detector. In one embodiment, a mercury cadmium telluride (Hg—Cd—Te) photodetector may be used to detect IR radiation. Other suitable detectors or detector arrays or combinations thereof may also be used.

According to an embodiment of the invention, the RES system may comprise a single detector with multiple filters instead of an array employing multiple detectors. The multiple filters may be moveable, such as spinning filters, to allow multiple components to be detected. In this regard, a single detector can be employed to detect a plurality of different exhaust components because each of the moveable filters is designed to allow only the wavelength band of interest by a particular exhaust component to pass to the detector. According to yet another embodiment of the invention, the RES system may comprise a spectrometer, or other detecting device which may be used to detect more than one component.

According to one embodiment, the RES system may comprise transfer optics 60 mounted in a manner to allow radiation from source 50 to be reflected to detector array 70 for analysis. Transfer optics 60 may comprise a mirror, flat mirror, lateral transfer mirror (LTM), vertical transfer mirror (VIM), retroflector, or other device. In one embodiment, transfer optics 60 may comprise a lateral transfer mirror to reflect radiation from source 50 along a path displaced laterally or vertically, depending on orientation, from the incident direction. Other configurations may be used.

In various embodiments, the RES system may comprise an imaging unit 80 to capture and/or record an image of vehicle 10 passing by (or through) the RES system in a known manner. Imaging unit 80 may be positioned to record an image of vehicle 10 at any predetermined number of locations. Imaging unit 80 may comprise, for example, a film camera, video camera, or digital camera. Other imaging devices may also be used.

In one embodiment, imaging unit 80 may record an image of the identification tag (e.g., license plate) of vehicle 10. Tag information may be processed, using a suitable processor 110 (described below), to provide additional information about the vehicle. For example, Motor Vehicle Department databases may be accessed to retrieve owner information, make, model type, model year, or other information. In some embodiments, this additional information may be incorporated into the emission sensing data analysis. For example, the make and model year of the vehicle may be used to determine input information for certain processing steps, including information such as whether the vehicle includes a carburetor or fuel injector, whether the car runs on diesel fuel or gasoline, etc.

According to an embodiment of the invention, the RES system may include a speed and acceleration detection unit 90. Preferably, the speed and/or acceleration of vehicle 10 may be measured as it passes through the RES system using speed and acceleration detection unit 90 in a known manner.

In one embodiment, speed and acceleration detection unit 90 may comprise an arrangement of laser beams or other light beams associated with timing circuitry. The laser or light beams may be arranged to traverse the path of vehicle 10 at various points. As vehicle 10 passes, it will cause interruptions in the laser or light beams. The times at which the beam interrupts occur may be used to calculate the vehicle's speed and/or acceleration.

Alternatively, the laser or light beams may be arranged to traverse the path of vehicle 10 at a single point in the vehicle's path. For example, radar systems may be used to determine vehicle speed and acceleration. Alternatively, transducers, piezoelectric elements, or other "drive over" detectors may be placed at locations in the roadway to monitor vehicle passage. Other methods of determining vehicle speed and/or acceleration may also be used or incorporated into the RES system. Speed and/or acceleration data may be input into processor 110 (described below) to help characterize vehicle operating conditions (e.g., accelerating or decelerating), or to determine which vehicle is to be associated with a particular sensor measurement. Other configurations and uses of speed and acceleration data are also possible.

Some embodiments of the invention may incorporate a thermal detection unit 100. In one embodiment, thermal detection unit 100 may comprise a non-contact thermometer system. For example, an IR thermometer may be used to optically detect the temperature of remote objects. Other temperature detection systems may also be used. Thermal detection unit 100 may, for example, be used to detect the temperature of portions of the vehicle passing through the RES system. Some embodiments may use direct sensing of the area of interest. For example, an IR thermometer may be aimed at the underside of a passing vehicle to detect the temperature(s) of vehicle components (e.g., engine, catalytic converter, muffler, etc.). Indirect sensing may also be used. For example, an IR thermometer may be aimed at the roadway to measure the heat of the passing vehicle which is reflected from the roadway surface.

Thermal information that is detected by thermal detection unit 100 may be used to indicate that an engine has just recently been started (e.g., the engine is "cold" or has not reached normal operating temperature). Such a cold engine reading may be used, for example, to initiate an alternative data processing routine. Certain embodiments of the invention may reduce the chance of a potentially misleading reading by also detecting the temperature of other portions of the vehicle. Other uses for collected thermal data are also possible.

Thermal detection of the exhaust plume of a vehicle, as well as ambient temperatures before, during, or after an emissions test, may also be used in connection with various aspects of the invention.

According to an embodiment of the invention, a pressure detection unit 130 may be utilized to obtain ambient pressure measurements before, during, or after an emissions test at various locations relative to the RES system. Pressure detection unit 130 may comprise a barometer or any other suitable pressure measurement equipment.

According to one embodiment of the invention, an identification tag on vehicle 10 may be read to identify the vehicle and associate particular sensed vehicle emission information with the vehicle. An identification tag (defined as a license plate above), may also comprise a transponder located on or within vehicle 10 (e.g., hung from a rear view mirror, placed on the dashboard, etc.), or that is integral within the vehicle (e.g., part of a global positioning system ("GPS"), located within the engine of the vehicle, or placed or mounted elsewhere). The transponder may transmit information about vehicle 10, including make and model of vehicle 10, engine characteristics, fuel type, the owner of vehicle 10, or other information which may be pertinent. According to an embodiment of the invention, a transponder may be used in connection with other functions. By way of example, a transponder may also be used in connection with a toll pass, whereby a driver can electronically pay tolls via the transponder without stopping the vehicle.

An identification tag may also comprise a tag or decal that requires a reader. By way of example, an identification tag may comprise a decal with identifying marks (e.g., bar codes, infrared markings, etc.) containing information about vehicle 10. The decal may be located outside vehicle 10, such as on a front or rear bumper, on the under-side of vehicle 10, or any other location on vehicle 10 where the decal may be suitably read. A reader may observe the decal and thereby obtain information about vehicle 10. One embodiment employs a bar code placed on the roof of vehicle 10, which can be read by a reader placed above vehicle 10.

A receiver may be used to obtain information form an identification tag. According to an embodiment of the invention, an antenna may receive signals transmitted from an identification tag containing a transponder. Any type of conventional receiver may be used to receive signals. According to an embodiment of the invention, one reader and/or receiver may be used in connection with multiple lanes. Based on the signal received or the decal read, a receiver or reader may determine in which lane a particular vehicle is located at a particular time.

Processor 110 (described below) may receive information about vehicle 10 from a reader and/or receiver. According to an embodiment of the invention, processor 110 may receive vehicle information. Vehicle information and information obtained by sensing vehicle emissions may be stored. Processor 110 may correlate vehicle information received from an identification tag with the results from vehicle emissions sensing. Processor 110 may update a vehicle record to account for the results obtained by processing vehicle emission data, such as information regarding whether a vehicle has passed or failed predetermined emissions criteria.

According to an embodiment of the invention, the RES system includes a processor 110. Processor 110 may comprise a suitable processing device such as, for example, a computer or other microprocessor, and may interface with any or all of the RES system components described herein. Processor 110 may have associated memory (not illustrated) for storing data, and, in some embodiments, may further interface to a database (not illustrated). Processor 110 may optionally employ software to accomplish desired analysis of collected and/or stored data in a known manner (subject to the improvements described herein). For example, and as briefly described above, software may be used to calculate the relative amounts of various exhaust gas constituents, concentrations of various exhaust gas constituents (e.g., HC, $CO_2$, $NO_x$, CO, etc.), the decay rate (e.g., dissipation in time) of the exhaust constituents, the opacity of the exhaust plume, the temperature, speed and acceleration of the vehicle, and to determine other desirable information as well.

According to an embodiment of the invention, and as described in greater detail below, processor 110 may calculate the relative amounts of various exhaust gas constituents by computing the ratio of the absorption for a particular exhaust gas constituent to the $CO_2$ gas constituent. For example, in one embodiment, source 50 may be configured to pass a beam of EM radiation through exhaust plume 30 of vehicle 10 as vehicle 10 passes by (or through) the RES system. The beam may be directed by transfer optics 60 to detector array 70 which may be configured to receive the radiation after it passes through exhaust plume 30. One or more filters (not illustrated) may be associated with detector array 70 to enable detector array 70 to determine the intensity of EM radiation having a particular wavelength or range of wavelengths. The wavelengths may be selected to correspond to wavelengths absorbed by molecular species of interest in an exhaust plume (e.g., hydrocarbons (HC), carbon monoxide (CO), carbon dioxide ($CO_2$) and nitrogen oxides ($NO_x$) such as NO and $NO_2$). One or more detector output voltages represent the intensity of the EM radiation measured by that detector.

These voltages are then input to processor 110. Processor 110 may calculate the difference between the known intensity of source 50 and the intensity detected by the detectors to determine the amount of absorption by the particular molecular species (based on predetermined wavelengths associated with that species). Based on the measured absorption(s), the number of molecules in the measurement path of one or more molecular species in the emissions may be determined in a known manner.

This exemplary method eliminates the need to calculate the total amount of exhaust plume present since the calculated ratios may provide sufficient information to identify vehicles which do not meet predetermined pollution criteria. Additionally, should the calculation of absolute concentrations of various components be required, an estimated value of $CO_2$ concentration based on vehicle type, fuel type, calibration readings or other methods, may be employed for this purpose.

Processor 110 may also comprise software to accomplish other data analysis functions. For example, vehicle emission data may be checked for running losses. Running losses may typically include emission readings due to fuel system leaks on a vehicle (e.g., leaky fuel tank filler cap, fuel line, etc.), blow-by emissions (e.g., crank case emissions blowing by the piston rings), emissions due to other vehicles in the vicinity, or other systematic losses.

Processor 110 may also include software to accomplish various vehicle owner notification functions. For example, the owner of a vehicle that has been recorded as being in compliance with certain predetermined emission levels may receive a notification. Coordination with local authorities may be arranged to grant vehicle owners a waiver or pass of local emission certification procedures upon receiving such a notification. Likewise, vehicles that fail to meet predetermined emission levels may receive a notification requiring the owner to remedy the non-compliance. Other data processing functions are also possible.

Processor 110 may further comprise software for executing the temperature and pressure compensation calculations described in detail below. According to an embodiment of the invention, processor 110 may further comprise a graphical user interface (GUI) for enabling a user (e.g., an emissions test administrator or other individual) to access, navigate, and otherwise utilize the various software processing functions described above. Other processing techniques may also be performed.

According to an embodiment of the invention, the RES system may further comprise a communicator 120. Communicator 120 may communicate information such as, for example, measured vehicle emissions and identification tag information from the RES system to various other locations (e.g., Motor Vehicle Departments, a central data repository, servers, etc.) for storage, processing, viewing, or other use in a known manner. Communicator 120 may transmit and/or receive information via a wire connection, such as cable or telephone line, or a wireless connection, such as by a radio, cellular, or satellite transmitter, or via any other type of suitable wireless communication.

In some embodiments, communicator 120 may comprise appropriate hardware and/or software to enable processor 110 to be accessed remotely over a network (not illustrated) via a communications link (not illustrated). The network may include any one or more of, for instance, the Internet, an intranet, a PAN (Personal Area Network), a LAN (Local Area Network), a WAN (Wide Area Network), a SAN (Storage Area Network), or a MAN (Metropolitan Area Network). The communications link may include any one or more of, for instance, a copper telephone line, a Digital Subscriber Line (DSL) connection, a Digital Data Service (DDS) connection, an Ethernet connection, an Integrated Services Digital Network (ISDN) line, an analog modem connection, a cable modem connection, or a wireless connection. In this regard, a user (e.g., an emissions test administrator or other individual) at a remote computer terminal can administer emissions tests, and/or analyze or process data. Thus, the RES system may, in various embodiments, comprise either manned or unmanned systems.

Calibration of the RES system (which will be discussed in greater detail below) may be enabled by a calibration cell (not illustrated), or through puff calibration (via a calibration gas canister), as known in the art.

As recited above, alternative RES system configurations may exist incorporating some or all of the aforementioned system components. Accordingly, the RES system illustrated in FIG. 1 should not be viewed as limiting.

As an example, in certain embodiments (not illustrated), source 50 and detector 70 may be placed on opposite sides of roadway 20. Various components of speed and acceleration detection unit 90 and thermal detection unit 100 may also be positioned on opposite sides of roadway 20.

In another embodiment (not illustrated), the RES system may comprise a compact, unmanned system that may be used for unattended monitoring of vehicle emissions data (also referred to as a "bunkered" unit). In such an embodiment, source 50, detector 70, imaging unit 80, processor 110, communicator 120, and various components of speed and acceleration detection unit 90 and thermal detection unit 100 may be housed together on a first side of roadway 20, while transfer optics 60 and various other components of speed and acceleration detection unit 90 and thermal detection unit 100 may be housed together on the opposite side of roadway 20. Other configurations are possible. Emissions and other measured data may be transmitted by communicator 120 as described in detail above.

Having provided a detailed description of the various components comprising the RES system, calculation and calibration methodologies are now addressed. To better understand how the calculation and calibration methodologies of the invention compensate for changes in ambient temperature and pressure, it is worthwhile to first provide a brief explanation of some previous calibration methods and how changes in these ambient conditions were neither previously recognized, nor appreciated. Two remote sensing products from Environmental Systems Products, Inc.—the AccuScan™ Remote Sensing Device (RSD) 3000 and the AccuScan™ Remote Sensing Device (RSD) 4000—will be discussed.

For the RSD 3000, calibration factors were determined by injecting known gas ratios into a path and obtaining raw gas ratio measurements of the ratios. The calibration factors comprised multipliers that would correct the measurement ratios (as defined by entered bottle ratios). Accordingly, as an example, basic field calibration for CO, HC, and NO may be represented as:

$$\text{RawCO/RawCO2*calCO=Corrected CO/CO}_2 \quad (1)$$

$$\text{RawHC/RawCO2*calHC=Corrected HC/CO}_2 \quad (2)$$

$$\text{RawNO/RawCO2*calNO=Corrected NO/CO}_2 \quad (3)$$

where:
"Raw" values represent measured gas amounts, typically channel voltages, or channel voltage ratioed to a reference channel voltage, that is then converted to a gas value through a stored curve relationship; and
"cal" values represent calibration factors.

One drawback associated with this calibration approach is that accuracy may be adversely affected if the measurement is not performed at the same temperature and pressure as those during calibration. Puff calibration should report perfect answers "by definition" since calibration multipliers yield the entered bottle ratios. Audit puffs of the same size and shape will yield accurate answers as long as ambient conditions do not change. As ambient $CO_2$ conditions vary, however, accuracy tends to degrade (i.e., the approach will not track varying ambient $CO_2$). In other words, with this approach, absorption coefficient variation effects are buried (accounted for) in the calibration at the calibration conditions.

For the RSD 4000, each gas measurement has its own individual calibration factor and is thus calibrated independently, rather than calculating a calibration factor for gas ratios (as described above with reference to the RSD 3000). The calibration factor (for each gas) is applied to raw voltage ratio measurements rather than to a gas curve output (i.e., the factor effects the input to the gas measurement curve rather than the output), as illustrated below:

$$n\text{CO}=\text{Gas Curve}_{CO} \text{ (measured voltage ratio}_{CO}\text{*calCO)} \quad (4)$$

$$n\text{CO}_2=\text{Gas Curve}_{CO2} \text{ (measured voltage ratio}_{CO2}\text{*calCO2)} \quad (5)$$

$$n\text{HC}=\text{Gas Curve}_{HC} \text{ (measured voltage ratio}_{HC}\text{*calHC)} \quad (6)$$

$$n\text{NO}=\text{Gas Curve}_{NO} \text{ (measured spectrometer value*calNO)} \quad (7)$$

where:
"n" is measured gas amount (e.g., number of molecules);
"Gas Curve" is the relationship between the gas amount and calibrated measured quantities;
"measured voltage ratio" is the analyte channel voltage divided by a Reference channel (non-absorbing) channel voltage;
"measured spectrometer value" is typically a pixel voltage from a spectrometer that corresponds to a known wavelength; and
"cal" is is a calibration factor that converts the measured voltage ratio to the Gas Curve relationship input, typically transmittance.

With the aforementioned approach, the measurement ratios may be correct for all gas amounts and the measurements may track ambient $CO_2$ variations provided that the gas curve relationships are correct. If the gas curves are incorrect, for example due to changes in ambient temperature and/or pressure, then measurement error will likely result.

Additionally, the effects of the RSD 4000 may be further clouded depending on how calibration factors (e.g., calCO, calCO$_2$, etc.) are determined, and in particular whether they are independently determined, or if they depend on other gases.

With puff calibration (e.g., with the RSD 4000), for example, the calibration factor for HC, represented as "calHC," is independently determined (depends only on HC). The calibration factor for CO, represented as "calCO," is independent for 1-point calibration, but depends on HC for 2-point calibration, as is known. The calibration factors for $CO_2$, represented as "calCO$_2$," and NO, represented as "calNO" depend on measured HC amount. HC dependency means that an HC measurement is used to determine the amount of the other gas in the puff (e.g., measured HC is multiplied by the $CO_2$/HC bottle value to determine measured $CO_2$). Effectively, this means that HC/$CO_2$ should always report correctly during calibration (like the RSD 3000), and that NO/HC ratios will report correctly.

For RSD 4000 puff calibration (without compensation for changes in temperature and pressure), the invention has recognized that the $HC/CO_2$ ratio will generally be accurate at calibration conditions but may not track well as ambient $CO_2$ changes. The invention has further recognized that the $CO/CO_2$ ratio will tend to measure low at low ambient pressures (e.g., at high altitude), and will tend to measure high at low temperatures. Additionally, the invention has recognized that the $NO/CO_2$ ratio will tend to measure high at low pressure (e.g., high altitude), and will tend to measure high at low temperatures. The foregoing assumes that the calibration is performed with puff gas injected at the ambient conditions, and not using a hot calibration extension tube, as gases injected into a hot extension tube may result in an improper calibration.

For RSD 4000 calibration using internal cell calibration in a known manner, calibration factors are independent (but note that NO isn't calibrated during a cell calibration). Other systems and calibration techniques are known and result in similar problems.

Having provided a brief overview of different calibration methodologies utilized by two different remote sensing products (the RSD 3000 and RSD 4000), and having identified the drawbacks of each based on the recognition that changes in ambient temperature and/or pressure do affect remote sensing of vehicle emissions, the approaches of the invention to compensate for such changes is now described. Although the following description will refer primarily to CO and $CO_2$, it should be understood that CO and $CO_2$ are used as exemplary gases only and, as such, the following description should not be viewed as limiting.

The invention disclosed herein recognizes and takes into account that absorption coefficients of CO and $CO_2$ change significantly as the temperature and pressure of the gases change. Accordingly, a fixed number of molecules of a gas in a measurement path will measure differently (e.g., provide a different transmittance) as ambient conditions, such as temperature and pressure, change. As such, a different gas curve (e.g., amount of molecules versus transmittance) exists at each ambient temperature and pressure condition. To the best of the inventor's knowledge, these facts were not previously appreciated fully and/or taken into account when remotely sensing the exhaust gas composition of motor vehicles.

According to an embodiment of the invention, magnitudes of approximate temperature and pressure sensitivities recognized (measured) for CO are 0.05% per degree Celsius, and 2.0% per psi, respectively. Magnitudes of approximate temperature and pressure sensitivities measured for $CO_2$ are 0.6% per degree Celsius, and 1.0% per psi, respectively. These sensitivities are not necessarily constant with the amount of gas in the measurement path and may vary with the bandwidth and center frequency of the optical filters selected for each gas measurement. For reference, the ambient operating ranges for pressure typically are approximately 1.0 psia to 14.7 psia (for an elevation ranging from sea level to approximately 8000 feet above sea level), while the ambient operating ranges for temperature typically are 0.0 degrees Celsius to 48.0 degrees Celsius. Additionally, for reference, typical factory conditions for which gas curves have been established are approximately 25.0 degrees Celsius and 13.6 psia (for an elevation of approximately 2500 feet above sea level).

The recognition of and compensation for these sensitivities signifies a departure from conventional calibration methodologies and calculation techniques. To account for the effect of the recognized sensitivities on emissions measurements, the invention employs novel calculation and calibration methodologies to compensate for the temperature and pressure effects.

The basic remote sensing measurements for vehicle emissions are gas ratios such as, for example, $CO/CO_2$, $HC/CO_2$, and $NO/CO_2$. Individual gas amounts, however, are measured to form the ratios. In accordance with various embodiments of the invention, calculation and calibration methodologies of the invention can be applied to individual gas amount measurements, to measured gas ratios, or to combinations of both. According to an embodiment of the invention, temperature and pressure compensation calculations may be enabled by a software program running on processor 110. During an emissions test, according to one implementation, at points in the program where CO or $CO_2$ gas amounts are calculated (e.g., generally every call to a CO and $CO_2$ gas polynomial function), the normally calculated gas amount may be modified by computing a correction amount for pressure and/or another correction amount for temperature.

Figure 2:
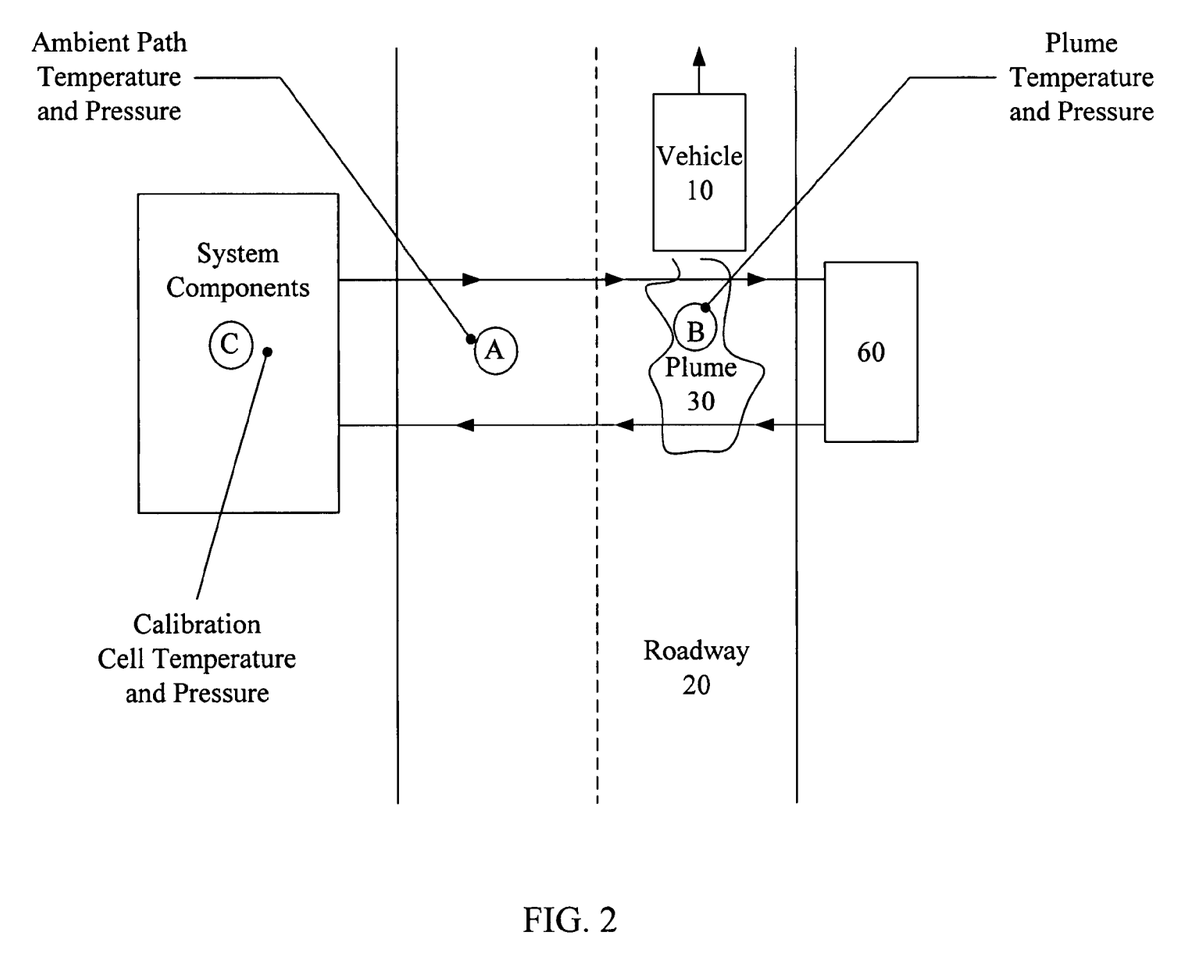
FIG. 2 is an exemplary illustration depicting various locations relative to a remote emissions sensing (RES) system where temperature and/or pressure measurements may be recorded, according to an embodiment of the invention.

As illustrated in FIG. 2, temperature and pressure measurements may be obtained before, during, or after an emissions test at various locations relative to the RES system using any suitable, known temperature and pressure measurement equipment and/or techniques (e.g., three-dimensional thermography techniques, barometer, etc.). These measurements may be obtained using, for example, thermal detection unit 100 and pressure detection unit 130 illustrated in FIG. 1. Ambient temperature and pressure may be obtained at a location "A" within the measurement path. Ambient temperature and pressure may also be measured at any number of locations relative to the RES system. Plume temperature and pressure may be measured at a location "B" within exhaust plume 30. Calibration cell temperature and pressure may be measured at a location "C" where a calibration cell is positioned (for example inside a housing). In one embodiment, the calibration cell may be housed within a "bunkered" unit along with various system components illustrated in FIG. 1.

Additional temperature and pressure measurements may be sampled either before, during, or after an emissions test from additional locations within (or relative to) the RES system. In certain embodiments, temperature and pressure measurements may be obtained from one or more (or all) of the ambient path (location "A"), exhaust plume (location "B"), or calibration cell (location "C"). In some embodiments, only pressure may be measured at one or more (or all) of these locations, only temperature may be measured at one or more (or all) of these locations, or any combinations of pressure and/or temperature or other ambient factors may be measured at one or more (or all) of these locations.

The ability to measure temperature and/or pressure at various locations relative to the RES system is important to account for a variety of different testing conditions. For example, the temperature (or pressure) of a gas in the calibration cell (e.g., within a housing in some embodiments) may be different from that in the ambient path (subject to weather conditions), which may be different from that in the exhaust plume (depending on size, type, and/or running condition of the vehicle).

According to one embodiment, pressure and temperature measurements may be acquired once at a vehicle emissions test site, and correction factors may be calculated only during calibration. Alternatively, pressure and temperature measurements may be monitored at a predetermined time interval and correction factors may be modified continuously, or they may be obtained as measurements are being made.

Figure 3:
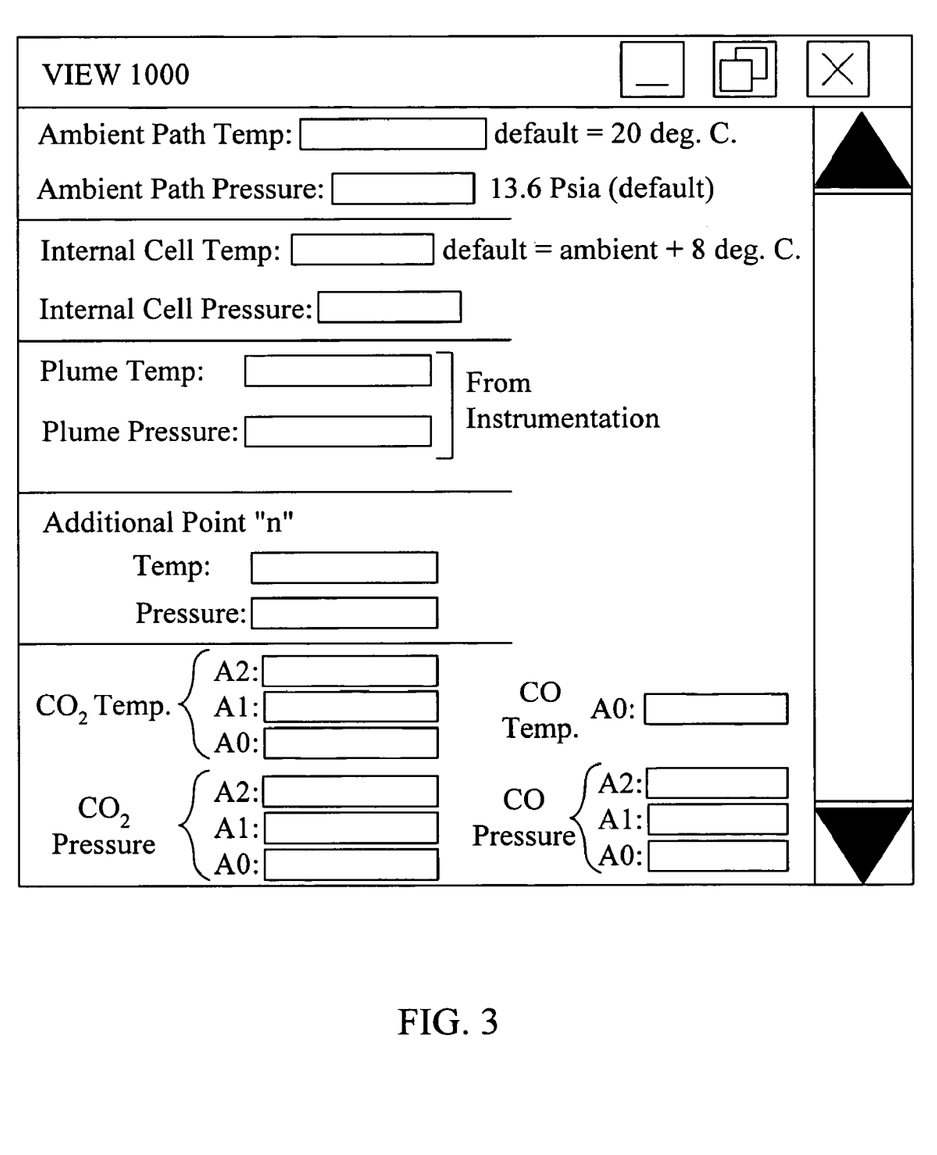
FIG. 3 is an exemplary illustration of a visual display screen that may be presented to a user, according to an embodiment of the invention.

According to an embodiment of the invention, manned or un-manned emissions testing may be enabled based on the configuration of the RES system as described in detail above, and illustrated in FIG. 1. A system administrator or other user accessing and/or executing an emissions testing program on processor 110 (FIG. 1), may, via a graphical user interface associated with processor 110, be presented with a display screen or view 1000, as illustrated in FIG. 3. Although the following description refers to Electrically Erasable Programmable Read-Only Memory (EEPROM) associated with processor 110, it should be understood that this is exemplary only, and not restrictive of the scope of the invention as any known types of memory may be used.

According to one embodiment, view 1000 may present various calibration options to a user and/or prompt a user for various inputs. For example, a user may be prompted to enter temperature and/or pressure measurements for the ambient path, for the internal calibration cell, or for an additional measurement location. Although view 1000 includes data fields for inputting plume temperature and pressure, these fields may, if measured in certain embodiments, be automatically populated with measurements obtained in real-time through the use of known temperature and pressure measurement equipment or techniques (e.g., three-dimensional thermography techniques, barometer, etc.) as recited above.

Default values may be entered in one or more of the data fields if actual measurements may not be obtained. For example, ambient path temperature, represented as "tamb" and measured in degrees Celsius (deg C.), may be set to a default value of 20.0 deg C. Ambient path pressure, represented as "Pamb" and measured in psia, may be set to a default value of 13.6 psia. Other default values may be used. As another example, the internal calibration cell temperature, represented as "tcell" and measured in degrees Celsius (deg C.), may be set to a default value of tamb+8.0 (deg C.). Other default values may be utilized. In one embodiment, additional data readings may be obtained from a local weather station via communicator 120 (FIG. 1). According to one embodiment of the invention, view 1000 may further comprise EEPROM fields for $CO_2$ temperature (A2, A1, A0), $CO_2$ pressure (A2, A1, A0), CO temperature (A0), and CO pressure (A2, A1, A0). Other fields may be provided.

According to an embodiment of the invention, and with reference to FIG. 1, the amount of CO, $CO_2$, or of any other selected gas constituent present in vehicle 10's exhaust plume 30 (in measurement path 40) may be determined using, among other components, source 50, transfer optics 60, detector 70, and processor 120, as described above. The measured amounts of CO and $CO_2$ are then corrected to account for the effects of ambient pressure and ambient temperature, using one of many possible approaches for pressure and temperature compensation.

For example, pressure correction values for both CO and $CO_2$ may be generated based, in part, on the ambient pressure, and temperature correction values for both CO and $CO_2$ may be generated based, in part, on the ambient temperature. The pressure correction value and temperature correction value for CO are then applied to the measured amount of CO to generate a corrected amount of CO. Likewise, the pressure correction value and temperature correction value for $CO_2$ are then applied to the measured amount of $CO_2$ to generate a corrected amount of $CO_2$. A gas ratio of the corrected amount of CO to the corrected amount of $CO_2$ may also then be determined.

One exemplary approach utilizes an empirically-determined polynomial correction curve that is a function of the gas measurement without correction. For example, for pressure, the pressure correction value may comprise a pressure correction curve polynomial value which represents a percentage (%) correction to a stored base curve required per unit pressure difference from a base pressure for which the stored base curve was established. The stored base curve may comprise a factory baseline curve of "gas amount versus transmittance" for a selected gas (e.g., CO, $CO_2$, etc.), and it may be stored in a memory or database associated with processor 110 (FIG. 1).

Similarly, for temperature, the temperature correction value may comprise a temperature correction curve polynomial value which represents a percentage (%) temperature correction to a stored base curve required per unit of temperature difference from a base temperature for which the stored base curve was established. The stored base curve may comprise a factory baseline curve of "gas amount versus transmittance" for a selected gas (e.g., CO, $CO_2$, etc.), and it may be stored in a memory or database associated with processor 110 (FIG. 1).

As an example, using CO and $CO_2$, EEPROM inputs may be pre-programmed or entered by a user, and may be utilized to calculate the CO and $CO_2$ correction curve polynomials as set forth below.

The CO correction curve polynomial for pressure may be computed using:

$$[(dn/n)/dp]_{CO}(nm_{CO}) = A2_{pCO} * nm_{CO}^2 + A1_{pCO} * nm_{CO} + A0_{pCO} \qquad (8)$$

where:
"$[(dn/n)/dp]_{CO}(nm_{CO})$" represents the percentage pressure correction to the CO base curve required per unit of pressure difference from baseline pressure conditions;
"nm" is the baseline gas amount measurement; and
"$A2_{pCO}$," "$A1_{pCO}$," and "$A0_{pCO}$" are empirically-determined coefficients.

The CO correction curve polynomial for temperature may be computed using:

$$[(dn/n)/dt]_{CO}(nm_{CO}) = A2_{tCO} * nm_{CO}^2 + A1_{tCO} * nm_{CO} + A0_{tCO} \qquad (9)$$

where:
"$[(dn/n)/dt]_{CO}(nm_{CO})$" represents the percentage temperature correction to the CO base curve required per unit of temperature difference from baseline temperature conditions;
"nm" is the baseline gas amount measurement; and
"$A2_{tCO}$," "$A1_{tCO}$," and "$A0_{tCO}$" are empirically-determined coefficients.

The $CO_2$ correction curve polynomial for pressure may be computed using:

$$[(dn/n)/dp]_{CO2}(nm_{CO2}) = A2_{pCO2} * nm_{CO2}^2 + A1_{pCO2} * nm_{CO2} + A0_{pCO2} \qquad (10)$$

where:
"$[(dn/n)/dp]_{CO2}(nm_{CO2})$" represents the percentage pressure correction to the $CO_2$ base curve required per unit of pressure difference from baseline pressure conditions;
"nm" is the baseline gas amount measurement; and
"$A2_{pCO2}$," "$A1_{pCO2}$," and "$A0_{pCO2}$" are empirically-determined coefficients.

The $CO_2$ correction curve polynomial for temperature may be computed using:

$$[(dt/n)/dt]_{CO2}(nm_{CO2}) = A2_{tCO2} * nm_{CO2}^2 + A1_{tCO2} * nm_{CO2} + A0_{tCO2} \qquad (11)$$

where:
"$[(dn/n)/dt]_{CO2}(nm_{CO2})$" represents the percentage temperature correction to the CO2 base curve required per unit of temperature difference from baseline temperature conditions;

"nm" is the baseline gas amount measurement; and

"$A2_{tCO2}$," "$A1_{tCO2}$," and "$A0_{tCO2}$" are empirically-determined coefficients.

The CO and $CO_2$ correction curve polynomial values may be used in the equations set forth below which are used to calculate the CO and $CO_2$ gas amounts corrected for changes in temperature and pressure.

The CO correction curve polynomial value may be used to calculate the corrected CO gas amount, as follows:

$$Tm_{CO} = Rm_{CO} * calCO \quad (12)$$

where:

"$Tm_{CO}$" is transmittance.

"$Rm_{CO}$" is measured CO channel voltage reduction ratio; channel voltage reduction ratio represents the amount of light absorption due to analyte gas present in the measurement path. When there is no analyte gas present, the voltage on the CO channel can be referred to as $V_{CO}$zero, and the Reference voltage as $V_{REF}$. The measurement ratio is $V_{CO}$zero divided by $V_{REF}$. When gas is present, the analyte voltage is less than $V_{CO}$zero while $V_{REF}$ remains the same.

"calCO" is a procedurally determined calibration factor that relates channel measurement to transmittance.

The value of "$Tm_{CO}$" from equation (12) may be used in the following equation:

$$nm_{CO} = polynomial_{CO}(1/Tm_{CO}) \quad (13)$$

where:

"$nm_{CO}$" is the measured amount of CO from a baseline gas relationship curve established at base temperature and base pressure; and "$polynomial_{CO}$" is typically an empirically determined power series that relates the gas amount to the inverse of optical transmittance.

The value of "$[(dn/n)/dp]_{CO}(nm_{CO})$" from equation (8) and the value of "$nm_{CO}$" from equation (13) may be used in the following equation:

$$\Delta np_{CO} = [(dn/n)/dp]_{CO}(nm_{CO}) * nm_{CO} * (Pbase - Pamb) \quad (14)$$

where:

"$\Delta np_{CO}$" is the gas amount correction effect from a baseline curve due to pressure;

"Pbase" is the pressure condition used to establish the baseline curve; and

"Pamb" is the existing barometric (ambient) pressure.

The value of "$[(dn/n)/dt]_{CO}(nm_{CO})$" from equation (9) and the value of "$nm_{CO}$" from equation (13) may be used in the following equation:

$$\Delta nt_{CO} = [(dn/n)/dt]_{CO}(nm_{CO}) * nm_{CO} * (tbase - tamb) \quad (15)$$

where:

"$\Delta nt_{CO}$" is the gas amount correction effect from a baseline curve due to temperature;

"tbase" is the temperature condition used to establish the baseline curve; and

"tamb" is the present ambient temperature.

The values of $\Delta np_{CO}$ from equation (14) and $\Delta nt_{CO}$ from equation (15) may be used in the following equation:

$$ncor_{CO} = nm_{CO} + \Delta np_{CO} + \Delta nt_{CO} \quad (16)$$

where:

"$ncor_{CO}$" is the CO corrected gas amount, that is corrected for changes in temperature and pressure.

The $CO_2$ correction curve polynomial value may be used to calculate the corrected $CO_2$ gas amount, as follows:

$$Tm_{CO2} = Rm_{CO2} * calCO_2 \quad (17)$$

where:

"$Tm_{CO2}$" is measured $CO_2$ optical transmittance;

"$Rm_{CO2}$" is measured $CO_2$ voltage ratio; and

"$calCO_2$" is a calibration factor that converts measured voltage ratio to transmittance.

The value of "$Tm_{CO2}$" from equation (17) may be used in the following equation:

$$nm_{CO2} = polynomial_{CO2}(1/Tm_{CO2}) \quad (18)$$

where:

"$nm_{CO2}$" is the measured amount of $CO_2$ from baseline gas relationship curve established at base temperature and base pressure; and "$polynomial_{CO2}$" is typically an empirically determined power series that relates the gas amount to the inverse of optical transmittance.

The value of "$[(dn/n)/dp]_{CO2}(nm_{CO2})$" from equation (10) and the value of "$nm_{CO2}$" from equation (18) may be used in the following equation:

$$\Delta np_{CO2} = [(dn/n)/dp]_{CO2}(nm_{CO2}) * i\, nm_{CO2} * (Pbase - Pamb) \quad (19)$$

where:

"$\Delta np_{CO2}$" is the gas amount correction effect from a baseline curve due to temperature;

"Pbase" is the pressure condition used to establish the baseline curve; and

"Pamb" is the existing barometric (ambient) pressure.

The value of "$[(dn/n)/dt]_{CO2}(nm_{CO2})$" from equation (11) and the value of "$nm_{CO2}$" from equation (18) may be used in the following equation:

$$\Delta nt_{CO2} = [(dn/n)/dt]_{CO2}(nm_{CO2}) * nm_{CO2} * (tbase - tamb) \quad (20)$$

where:

"$\Delta nt_{CO2}$" is the gas amount correction effect from a baseline curve due to temperature;

"tbase" is the temperature condition used to establish the baseline curve; and

"tamb" is the present ambient temperature.

The determined values of $\Delta np_{CO2}$ from equation (19) and $\Delta nt_{CO2}$ from equation (20) are used in the following equation:

$$ncor_{CO2} = nm_{CO2} + \Delta np_{CO2} + \Delta nt_{CO2} \quad (21)$$

where:

"$ncor_{CO2}$" is the $CO_2$ corrected gas amount, that is corrected for changes in temperature and pressure.

The foregoing example represents one of many embodiments of pressure and temperature correction recognizing that the basic gas measurement is a function of transmittance, gas temperature, and gas pressure.

According to an embodiment of the invention, $CO_2$ cell calibration may be performed as previously known in the art, with the exception that calibration cell pressure and temperature may be used rather than ambient pressure (Pamb) and ambient temperature (tamb). Since the calibration gas cell is sealed, the ideal gas law is used to determine the cell pressure as a function of the present cell temperature and its conditions when it was filled:

$$Pcell = tcell\,(deg\,K) * (Pfill/tfill) \quad (22)$$

where:

"tcell" is cell temperature at calibration;

"Pfill" is the pressure of the calibration gas cell when it was sealed; and

"tfill" is the temperature of the calibration gas cell when it was sealed.

Figure 4:
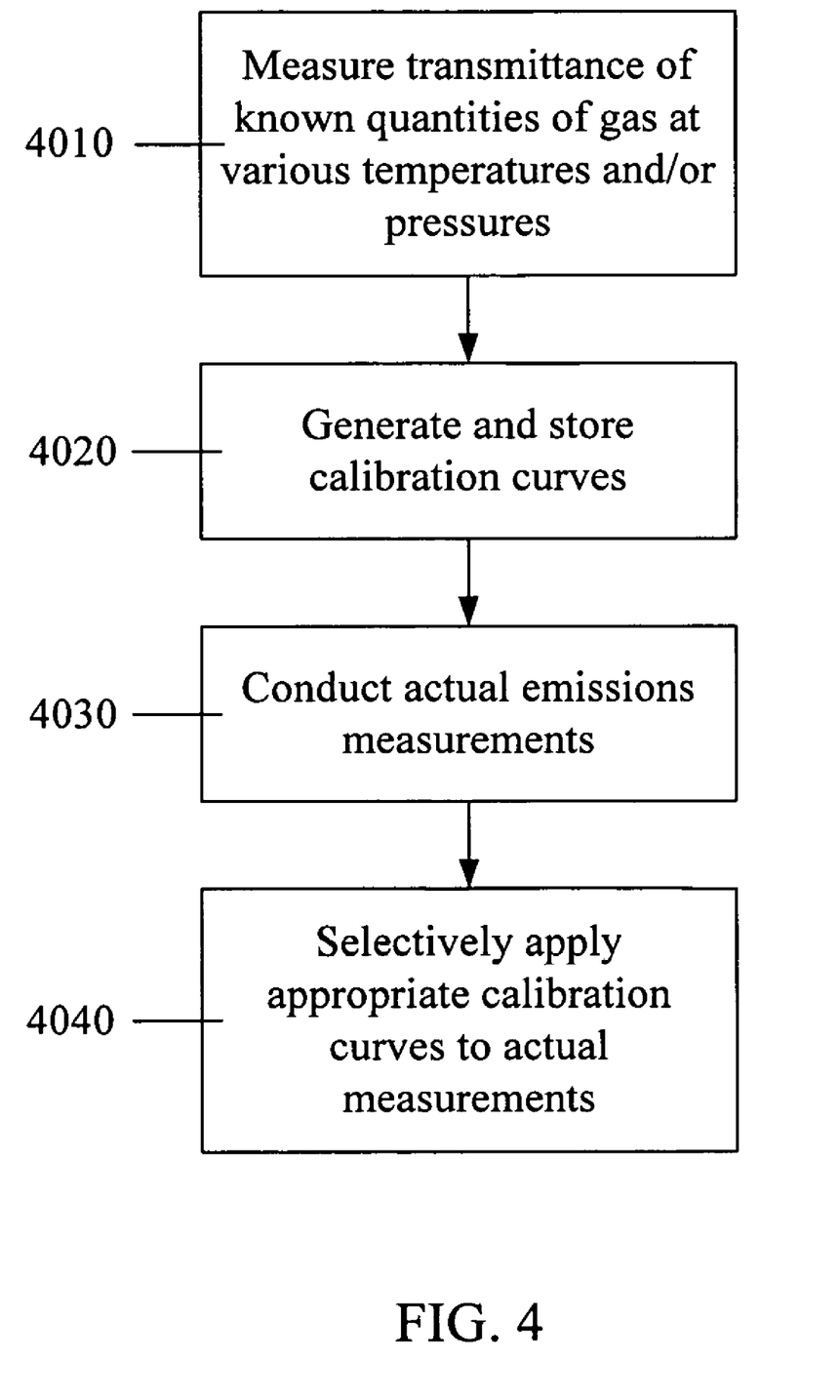
FIG. 4 illustrates a flowchart for processing according to the invention, in one regard.

In addition to the foregoing description, FIG. 4 illustrates a flowchart of processing according to the invention, in one regard. The following operations may be accomplished using some or all of the aspects of the invention as set forth in the foregoing description and accompanying drawing figures.

In an operation 4010, transmittance measurements for known quantities of gases (e.g., CO and $CO_2$) at various temperatures and/or pressures may be obtained. These measurements may be obtained in a factory setting, or alternatively, at various locations relative to an RES system (e.g., FIGS. 1-2).

In an operation 4020, calibration or compensation curves (e.g., number of molecules versus transmittance) for gases measured in operation 4010 may be generated and stored.

In an operation 4030, temperature and/or pressure measurements may be acquired during an emissions test at various locations (e.g., FIG. 2) relative to the RES system using any suitable, known temperature and pressure measurement equipment and/or techniques (e.g., three-dimensional thermography techniques, barometer, etc.). For example, ambient temperature and/or pressure may be obtained at a point within the measurement path. Ambient temperature and/or pressure may also be measured at any number of locations relative to the RES system. Plume temperature and/or pressure may be measured at a point "B" within the exhaust plume of a vehicle being tested. Calibration cell temperature and/or pressure may be obtained at a location where the calibration cell is positioned (for example inside a housing). The ability to measure temperature and/or pressure at various locations relative to the RES system is important to account for a variety of different testing conditions. For example, the temperature (or pressure) of a gas in the calibration cell (e.g., within a housing in some embodiments) may be different from that in the ambient path (subject to weather conditions), which may be different from that in the exhaust plume (depending on size, type, and/or running condition of the vehicle).

In an operation 4040, a correction or calibration factor may be applied to transmittance measurements for a gas acquired during an emissions test by, for example, selectively applying those temperature and/or pressure calibration curves (generated in operation 4020) that correspond to the temperature and/or pressure measured during the emissions test (in operation 4030).

Figure 5:
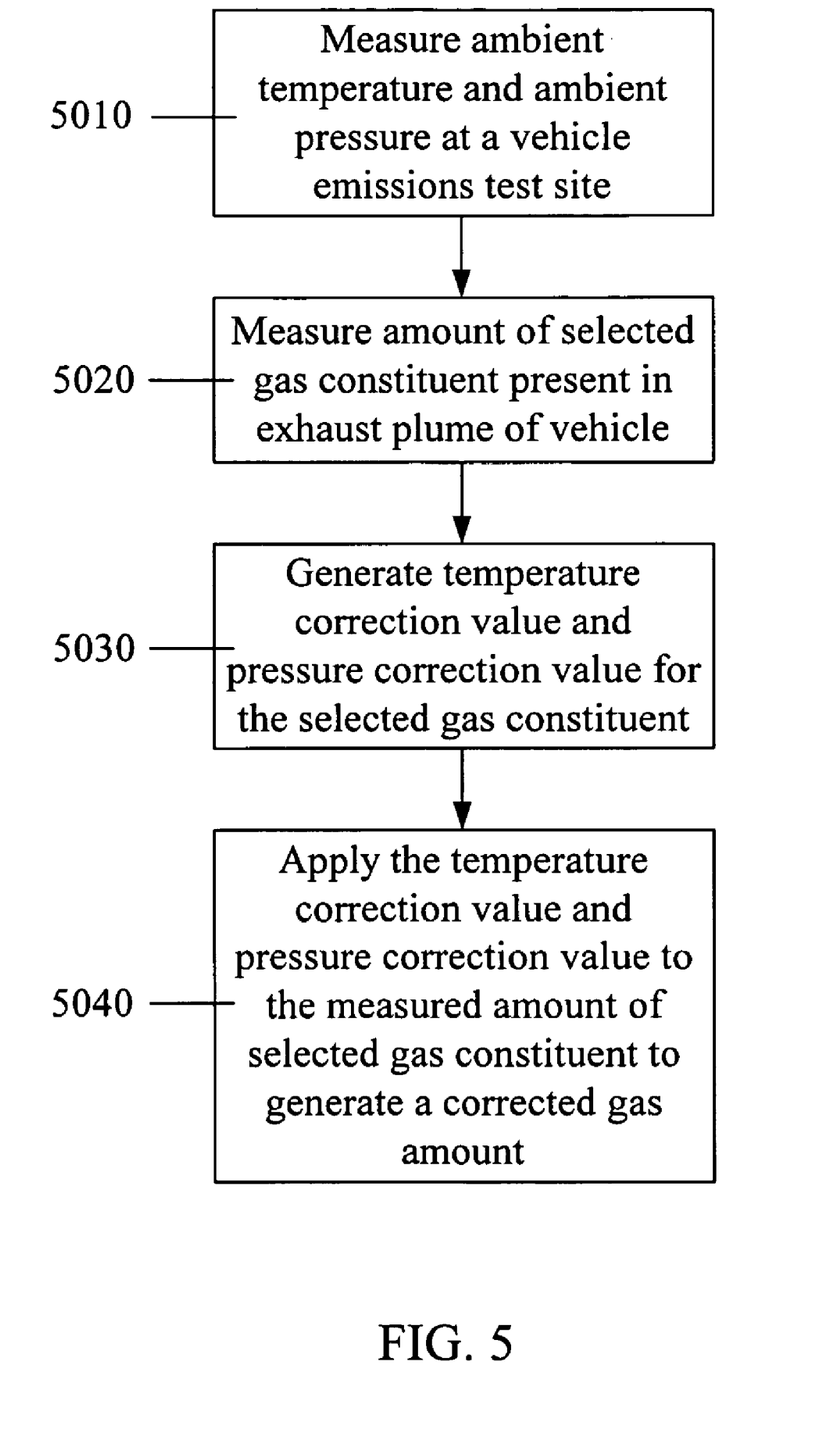
FIG. 5 illustrates a flowchart for processing according to the invention, in one regard.

FIG. 5 illustrates a flowchart of processing according to the invention, in one regard. The following operations may be accomplished using some or all of the aspects of the invention as set forth in the foregoing description and accompanying drawing figures.

In an operation 5010, ambient temperature and ambient pressure may be measured at a vehicle emissions test site. The temperature and pressure measurements may be obtained before, during, or after an emissions test at various locations relative to the RES system using any suitable, known temperature and pressure measurement equipment and/or techniques (e.g., three-dimensional thermography techniques, barometer, etc.).

In an operation 5020, an amount of a selected gas constituent (e.g., CO, $CO_2$, HC, $NO_x$, $NH_3$, $SO_2$, etc.) present in the exhaust plume of a passing motor vehicle may be measured utilizing the RES components as described above.

In an operation 5030, a temperature correction value may be generated for the selected gas constituent based, in part, on the ambient temperature measured in operation 5010. In one embodiment, the temperature correction value may comprise a temperature correction curve polynomial value which represents a percentage (%) temperature correction to a stored base curve required per unit of temperature difference from a base temperature for which the stored base curve was established. In one embodiment, the base temperature for which the stored base curve is established may be approximately 25.0 degrees Celsius.

Additionally, in operation 5030 (or in a separate operation), a pressure correction value may be generated for the selected gas constituent based, in part, on the ambient pressure measured in operation 5010. In one embodiment, the pressure correction value may comprise a pressure correction curve polynomial value which represents a percentage (%) pressure correction to a stored base curve required per unit of pressure difference from the base pressure for which the stored base curve was established. In one embodiment, the base pressure for which the stored base curve is established may be approximately 13.6 psia.

In an operation 5040, the temperature correction value and the pressure correction value may be applied to the measured amount of the selected gas constituent to generate a corrected gas amount for the selected gas constituent using the calculation methodologies set forth in detail above.

Other embodiments, uses and advantages of the invention will be apparent to those skilled in the art from consideration of the specification and practice of the invention disclosed herein. For example, although the Specification refers primarily to CO and $CO_2$, it should be understood that CO and $CO_2$ are used as exemplary gases only and, as such, the embodiments of the invention are equally applicable to any exhaust gas constituent from any vehicle including, but not limited to, HC, $NO_x$, $NH_3$, $SO_2$, etc. Additionally, although the embodiments of the invention have been described herein with regard to remote emissions sensing, it should be recognized that the techniques (or methodologies) invention may be applied to other types of emissions sensing.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A method of correcting for an effect of temperature and pressure on one or more exhaust gas constituents of an exhaust plume, in a measurement path, emitted from a motor vehicle during an emissions test, the method comprising:

measuring ambient temperature and ambient pressure at a vehicle emissions test site;

measuring, from an exhaust plume of a passing motor vehicle, an amount of a selected gas constituent present in the exhaust plume in the measurement path;

generating, for the selected gas constituent, a temperature correction value based, in part, on the measured ambient temperature, wherein the temperature correction value is determined from a temperature correction proportionality coefficient that is defined by a temperature correction curve polynomial function that describes the temperature correction proportionality coefficient as a function of the measured amount of the selected gas constituent, and wherein the step of generating the temperature correction value comprises:

(i) determining the temperature correction proportionality coefficient as a function of the measured amount of the selected gas constituent according to the temperature correction polynomial function; and (ii) generating the temperature correction value by multiplying the temperature correction proportionality coefficient by the temperature difference between a base temperature and the measured ambient temperature;

generating, for the selected gas constituent, a pressure correction value based, in part, on the measured ambient pressure, wherein the pressure correction value is determined from a pressure correction proportionality coefficient that is defined by a pressure correction curve polynomial function that describes the pressure correction proportionality coefficient as a function of the measured amount of the selected gas constituent, and wherein the step of generating the pressure correction value comprises:
  (i) determining the pressure correction proportionality coefficient as a function of the measured amount of the selected gas constituent according to the pressure correction polynomial function; and
  (ii) generating the pressure correction value by multiplying the pressure correction proportionality coefficient by the pressure difference between a base pressure and the measured ambient pressure;
applying the temperature correction value and the pressure correction value to the measured amount of the selected gas constituent to generate a corrected gas amount for the selected gas constituent; and
storing the corrected gas amount generated for the selected gas constituent in a memory.

2. The method of claim 1, further comprising:
measuring, from the exhaust plume of the passing motor vehicle, an amount of $CO_2$ present in the exhaust plume;
generating, for the measured amount of $CO_2$, a temperature correction value based, in part, on the measured ambient temperature;
generating, for the measured amount of $CO_2$, a pressure correction value based, in part, on the measured ambient pressure;
applying the temperature correction value and the pressure correction value to the measured amount of $CO_2$ to generate a corrected amount of $CO_2$; and
generating a gas ratio of absorption for the corrected gas amount for the selected gas constituent to the corrected amount of $CO_2$.

3. The method of claim 2, wherein the selected gas constituent comprises one of CO, HG, or NO.

4. The method of claim 1, wherein the step of measuring ambient temperature and ambient pressure at a vehicle emissions test site further comprises:
measuring ambient temperature and ambient pressure in the measurement path prior to commencing an emissions test.

5. The method of claim 1, wherein the step of measuring an amount of a selected gas constituent present in the exhaust plume in the measurement path further comprises:
emitting a radiation beam of known intensity from at least one radiation source across a vehicle travel lane and through the exhaust plume of the passing motor vehicle, the radiation beam having a wavelength corresponding to a wavelength absorbed by the selected gas constituent;
receiving the radiation beam via at least one radiation detector;
outputting a detector output voltage representing the intensity of the received radiation beam to at least one processor, the at least one processor calculating the difference between the known intensity of the radiation beam and the intensity detected by the at least one detector to measure an amount of absorption by the selected gas constituent; and
determining, based on the measured absorption, the amount of the selected gas constituent in the measurement path.

6. A system for correcting for an effect of temperature and pressure on one or more exhaust gas constituents of an exhaust plume, in a measurement path, emitted from a motor vehicle during an emissions test, comprising:
means for measuring ambient temperature and ambient pressure at a vehicle emissions test site;
means for measuring, from an exhaust plume of a passing motor vehicle, an amount of a selected gas constituent present in the exhaust plume in the measurement path;
means for generating, for the selected gas constituent, a temperature correction value based, in part, on the measured ambient temperature, wherein the temperature correction value is determined from a temperature correction proportionality coefficient that is defined by a temperature correction curve polynomial function that describes the temperature correction proportionality coefficient as a function of the measured amount of the selected gas constituent, and wherein generating the temperature correction value comprises:
  (i) determining the temperature correction proportionality coefficient as a function of the measured amount of the selected gas constituent according to the temperature correction polynomial function; and
  (ii) generating the temperature correction value by multiplying the temperature correction proportionality coefficient by the temperature difference between a base temperature and the measured ambient temperature;
means for generating, for the selected gas constituent, a pressure correction value based, in part, on the measured ambient pressure, wherein the pressure correction value is determined from a pressure correction proportionality coefficient that is defined by a pressure correction curve polynomial function that describes the pressure correction proportionality coefficient as a function of the measured amount of the selected gas constituent, and wherein generating the pressure correction value comprises:
  (i) determining the pressure correction proportionality coefficient as a function of the measured amount of the selected gas constituent according to the pressure correction polynomial function; and
  (ii) generating the pressure correction value by multiplying the pressure correction proportionality coefficient by the pressure difference between a base pressure and the measured ambient pressure;
means for applying the temperature correction value and the pressure correction value to the measured amount of the selected gas constituent to generate a corrected gas amount for the selected gas constituent; and
means for storing the corrected gas amount generated for the selected gas constituent for further processing.

* * * * *